(12) United States Patent
Wolf et al.

(10) Patent No.: US 10,828,411 B2
(45) Date of Patent: Nov. 10, 2020

(54) APPARATUS FOR CARRYING OUT A TIDAL PERITONEAL DIALYSIS TREATMENT

(71) Applicant: FRESENIUS MEDICAL CARE DEUTSCHLAND GMBH, Bad Homburg (DE)

(72) Inventors: Klaus Wolf, Arnstein-Muedesheim (DE); Erik Griessmann, Schweinfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 74 days.

(21) Appl. No.: 15/509,011

(22) PCT Filed: Sep. 3, 2015

(86) PCT No.: PCT/EP2015/001783
§ 371 (c)(1),
(2) Date: Mar. 6, 2017

(87) PCT Pub. No.: WO2016/034287
PCT Pub. Date: Mar. 10, 2016

(65) Prior Publication Data
US 2017/0274130 A1 Sep. 28, 2017

(30) Foreign Application Priority Data
Sep. 5, 2014 (DE) .......................... 10 2014 013 229

(51) Int. Cl.
*A61M 1/28* (2006.01)
(52) U.S. Cl.
CPC ............ *A61M 1/282* (2014.02); *A61M 1/284* (2014.02); *A61M 2205/3334* (2013.01); *A61M 2205/3344* (2013.01); *A61M 2205/50* (2013.01)

(58) Field of Classification Search
CPC .................. A61M 1/282; A61M 1/284; A61M 2205/3334; A61M 2205/3344; A61M 2205/50
See application file for complete search history.

(56) References Cited

U.S. PATENT DOCUMENTS

| 5,324,422 A  * | 6/1994 | Colleran ................. A61M 1/28 |
| | | 210/143 |
| 2010/0137782 A1* | 6/2010 | Jansson ................. A61M 1/281 |
| | | 604/28 |

(Continued)

FOREIGN PATENT DOCUMENTS

| DE | 602004011981 | 3/2009 |
| EP | 0498382 | 8/1992 |

(Continued)

*Primary Examiner* — Jenna Zhang
(74) *Attorney, Agent, or Firm* — Jacobson Holman PLLC

(57) ABSTRACT

An apparatus for a tidal peritoneal dialysis treatment that includes a sequence of cycles each having a filling period, a dwell period, and a drain period, includes a cycler and a processor. The cycler fills a patient's abdominal cavity with a specific inflow volume of fresh dialysis solution up to a specific patient volume in the filling period, and empties consumed dialysis solution from the cavity up to a specific tidal outflow target in the drain period. The processor controls the cycler in an operating mode such that the drain period is ended before reaching the tidal outflow target, so that a permitted residual volume remains in the abdominal cavity. A switch is made to a filling period, with the filling period being carried out such that the filling volume of the patient lies at a permitted patient volume above the specific patient volume on completion of the filling period.

16 Claims, 2 Drawing Sheets

(56) References Cited

U.S. PATENT DOCUMENTS

| | | | | |
|---|---|---|---|---|
| 2010/0191180 A1* | 7/2010 | Childers | ............... | A61M 1/28 604/29 |
| 2010/0191181 A1* | 7/2010 | Childers | ............... | A61M 1/28 604/29 |
| 2011/0071465 A1* | 3/2011 | Wang | ............... | G16H 20/40 604/67 |
| 2011/0186517 A1* | 8/2011 | Hedmann | ............... | A61M 1/287 210/645 |
| 2011/0303598 A1* | 12/2011 | Lo | ............... | A61M 1/16 210/188 |
| 2012/0071815 A1* | 3/2012 | Childers | ............... | A61M 1/28 604/29 |
| 2012/0123322 A1* | 5/2012 | Scarpaci | ............... | A61M 1/28 604/29 |
| 2012/0143124 A1* | 6/2012 | Mastalli | ............... | A61M 1/28 604/29 |
| 2013/0006171 A1* | 1/2013 | Griessmann | ............... | A61M 1/166 604/29 |
| 2013/0156847 A1* | 6/2013 | Ichim | ............... | C12N 5/0605 424/450 |
| 2013/0165847 A1* | 6/2013 | Scarpaci | ............... | A61M 1/288 604/28 |
| 2013/0184638 A1* | 7/2013 | Scarpaci | ............... | A61M 1/166 604/28 |
| 2015/0231320 A1* | 8/2015 | Helmore | ............... | A61M 1/281 604/29 |
| 2016/0101278 A1* | 4/2016 | Norris | ............... | A61M 1/166 604/29 |

FOREIGN PATENT DOCUMENTS

| | | |
|---|---|---|
| EP | 1691863 | 8/2006 |
| WO | WO 2005/035023 | 4/2005 |
| WO | WO 2012/036836 | 3/2012 |

* cited by examiner

APPARATUS FOR CARRYING OUT A TIDAL PERITONEAL DIALYSIS TREATMENT

BACKGROUND OF THE INVENTION

1. Field of the Invention

The present invention relates to an apparatus for carrying out a tidal peritoneal dialysis treatment of a patient, wherein the dialysis treatment comprises a sequence of cycles which each have a filling period, a dwell period and a drain period, wherein the apparatus has at least one cycler which is suitable for filling the abdominal cavity of the patient with a specific inflow volume of fresh dialysis solution up to a reaching of a specific patient volume in the filling period and for emptying consumed dialysis solution from the abdominal cavity of the patient up to a reaching of a specific tidal outflow target in the drain period.

2. Description of Related Art

In the course of peritoneal dialysis, a dialysis solution is introduced into the abdominal cavity of the patient to be treated during a filling period. Said dialysis solution remains there for a dwell period in which a mass transfer takes place with the blood of the patient, whereby the blood is purified. At the end of the dwell period, the dialysis solution is emptied again during the drain period.

This procedure is repeated over a plurality of sequentially following cycles. The so-called cycler serves this purpose; it comprises one or more pumps which carry out the successive filling and emptying of dialysis solution into and out of the abdominal cavity.

Peritoneal dialysis methods are known from the prior art in which the dialysis solution is completely emptied during the drain period. The so-called tidal peritoneal dialysis treatment is furthermore known in which an initial filling volume is introduced, but in each case only a portion of this filling volume is emptied during the drain periods, i.e. a certain volume of dialysis solution always remains in the patient until the treatment is completely concluded. The cycler is thus operated such that the drain period takes place up to a reaching of a specific tidal outflow target, i.e. for so long until a specific volume of dialysis solution has been removed from the abdominal cavity. This specific removed volume of consumed dialysis solution is called a tidal outflow target within the framework of the present invention.

FIG. 4 shows the time sequence of the steps of a known tidal peritoneal dialysis treatment. The ordinate shows the volume of dialysis solution in the patient; the abscissa shows the time.

At the start, in step 1, the filling of the abdominal cavity with a volume of dialysis solution takes place. After the end of a specific dwell period V, consumed dialysis solution is emptied from the abdominal cavity during the drain period A up to the reaching of a specific tidal outflow target. As can be seen from FIG. 4, approximately 1600 ml (2700 ml-1100 ml) are emptied in the course of the drain period A in the example shown here. In the example, the tidal outflow target is thus 1600 ml. A further filling of the abdominal cavity with a specific inflow volume (here likewise 1600 ml) takes place subsequent to the drain period A during the filling period F until a specific patient volume, i.e. a specific volume of dialysis solution, has been reached in the abdominal cavity. In the example shown, this volume amounts to 2700 ml.

The dialysis solution is completely emptied from the abdominal cavity after carrying out a number of cycles (step 2).

In the tidal prescription, the exchange volume, i.e. the volume of dialysis solution removed from the patient in the course of the drain period, is preset (volume-controlled outflow). A fixedly predefined volume is thus emptied into the drain. As can further be seen from FIG. 4, this volume is reduced in comparison with the volume exchanged in the base cycle (steps 1 and 2). This is used in many applications for reasons of alarm minimization or of alarm avoidance during the APD treatment (APD=automated peritoneal dialysis) which is usually at night.

The reduction of the exchange volumes of the individual tidal cycles effects a reduction in the exchange quantities of the dialysis solution. In order nevertheless to be able to dispense a predefined volume of dialysis solution during a specific treatment time, the individual dwell periods V are kept short and the number of cycles is selected as correspondingly large. In the known tidal peritoneal dialysis treatment, there is thus a compromise between short dwell times, low outflow quantities and dispensed dialysis solution. This compromise has a direct effect on the dialysis efficiency.

A peritoneal dialysis treatment is known from EP 1 691 863 B1 in which a parameter is detected during the drain period which is representative for the drain rate. The drain period is ended on detection of a substantial change in the value of this parameter and a switch to a filling period is made. The described procedure can have the result that a residual volume of fresh dialysis solution is still left at the end of the treatment, i.e. at the end of the treatment time, so that a further cycle has to be added to the treatment in order also to be able to use this solution. This procedure is furthermore as a rule accompanied by a shortening of the dwell time of the dialysis solution in the abdominal cavity.

If the tidal outflow target cannot be reached, the inflow volume of the following cycle is accordingly also reduced to avoid an accumulation of volumes in the patient. The reduction of the inflow volume does not result in a complete utilization of the dialysis solution with a predefined treatment time, i.e. the total provided dialysis solution cannot be dispensed.

SUMMARY OF THE INVENTION

It is the underlying object of the present invention to further develop an apparatus of the initially named kind such that a large exchange volume, i.e. a large volume of the dialysis solution supplied to the patient, can be dispensed in the course of the treatment.

This object is achieved by an apparatus having the features described herein.

Provision is accordingly made that the apparatus configured as a peritoneal dialyzer furthermore has at least one processor which controls the cycler in at least one operating mode such that the drain period is ended before reaching the tidal outflow target and then a switch is made to a filling period so that a permitted residual volume remains in the abdominal cavity and so that the filling period is carried out such that the filling volume of the patient lies at a permitted patient volume above the specific patient volume on the completion of the filling period.

The tidal outflow target and/or the specific inflow volume and/or the specific patient volume are fixedly predefined values or are values which can be varied on the user side. They are preferably stored in one or more memories of the unit.

The volume management in accordance with the invention thus provides that the drain period is ended when an outflow volume limit or an outflow volume range has been reached. This limit/range is above the tidal outflow target. Emptying thus does not take place for so long in at least one operating mode of the apparatus until the prescribed tidal outflow target of a cycle has been reached, but the drain period is rather already previously aborted and a switch made to a new filling period.

Furthermore, in a filling period following on from this, a maximum patient volume increased with respect to the specific patient volume, i.e. an increased maximum volume of dialysis solution in the patient, is tolerated. The permitted patient volume is thus above the specific patient volume of a customary tidal peritoneal dialysis treatment. With respect to the initially named example, the specific patient volume lies at 2700 ml and the permitted patient volume at 3000 ml, for example.

In this manner, both high exchange volumes (tidal outflow volumes) and the aim of the alarm avoidance or of the alarm reduction can be achieved.

Provision is preferably made that the permitted residual volume and/or the permitted patient volume can be adjusted. Since in accordance with the invention the drain period is aborted before reaching the tidal outflow target in at least one operating mode, an increased volume of dialysis solution remaining in the abdominal cavity results; this volume is called a residual volume within the framework of the invention.

It is particularly advantageous if the permitted residual volume and the permitted patient volume can be set independently of one another. An independent and individual adjustability of these values allows an ideal adaptation of the treatment to the patient.

Provision is preferably made that the aborting of the drain period in accordance with the invention and the subsequent filling up to a permitted patient volume, i.e. the volume management in accordance with the invention, is only used as required. This can be the case if it is found that the tidal outflow target is not reached or is not reached in a specific time period from the start of the drain period.

It is thus conceivable that the processor is configured such that the selection of the operating mode depends on the reaching of the tidal outflow target. If it is found that the tidal outflow target is not reached or is not reached within a specific time period, the operating mode in accordance with the invention can be selected in which the drain period is aborted before the reaching of the tidal outflow target and the filling takes place in the filling period up to a permitted patient volume above the specific patient volume. If it is, however, found that the tidal outflow time is reached, the apparatus can be carried out without these measures, i.e. conventionally as shown in FIG. 4. In this case, the switching over from the drain period to the filling period does not take place before the reaching of the tidal outflow volume, but rather on the reaching thereof and the filling in the filling period does not take place above the specific patient volume, but on the reaching thereof.

Provision is made in an embodiment of the invention that the processor is configured such that the time at which the drain period is ended depends on at least one parameter. This parameter, for whose measurement at least one sensor can be present, can be the reached drain volume and/or the flow rate of the dialysis solution during the drain period and the pressure in the abdominal cavity of the patient.

The processor can be configured such that the switchover value at which the drain period is ended amounts to a specific percentage of the tidal outflow target, i.e. of the volume of dialysis solution or of the specific inflow volume to be removed during a drain period in accordance with the prescription, with provision preferably being made that the percentage lies in the range from 0 to 60%, and preferably in the range from 10 to 50%, of the tidal outflow target or of the specific inflow volume. If the value of 10% is assumed and if the tidal outflow target amounts to 1 l, the limit value adopts the value of 100 ml. This means that with an outflow volume of 900 ml (1 l-100 ml), i.e. 100 ml before the reaching of the tidal outflow target, a switchover is made.

A range from 0 to 60%, and preferably in the range from 10 to 50%, of the highest inflow volume can thus be provided, for example, for the lower switchover point at which the drain period is aborted. With an inflow volume or with a tidal outflow target of 1 l, the switchover point can therefore lie in a range from 100 to 500 ml of the provided drain volume. A switchover can thus be made, i.e. the drain period can be ended, when 500 ml to 900 ml of consumed dialysis solution was removed during the drain period.

Furthermore, the processor can be configured such that the permitted patient volume or the volume added within the course of the filling period lies in the range from above 100 to 150%, preferably in the range from above 100 to 120%, and particularly preferably in the range from above 100 to 130%, of the specific patient volume or of the specific inflow volume. A maximum permitted volume of above 100% (100%=no additional patient volume is tolerated) up to 150% is tolerated for the upper range, i.e. for the upper switchover point. I.e. with a prescribed inflow volume of 1 l, further dialysis solution up to an accumulated inflow volume of max. 1.5 l can be added in this embodiment of the invention.

The present invention furthermore relates to a method for carrying out a tidal peritoneal dialysis treatment which comprises a sequence of cycles which respectively have a filling period, a dwell period and a drain period, with the filling of the abdominal cavity of the patient with a specific inflow volume of fresh dialysis solution up to a reaching of a specific patient volume taking place during the filling period in normal operation and with the emptying of consumed dialysis solution from the abdominal cavity of the patient up to a reaching of a specific tidal outflow target taking place in the drain period, with the drain period being ended before reaching the tidal outflow target in at least one operation mode differing from normal operation so that a permitted residual volume remains in the abdominal cavity and then a switchover into a filling period takes place and so that the filling period is carried out such that the filling volume of the patient with dialysis solution lies above the specific patient volume on an ending of the filling period at a permitted patient volume.

Provision is preferably made that the permitted residual volume and/or the permitted patient volume can be adjusted. It is advantageous if the permitted residual volume and the permitted patient volume can be set independently of one another. This can apply accordingly to one or both switchover points (lower switchover point from the drain period to the filling period and/or upper switchover point from the filling period to the dwell period).

In a further embodiment of the invention, the selection of the operating mode depends on the reaching of the tidal outflow target. If the tidal outflow target is reached or if it is reached within a specific time period, the aborting of the drain period and an increase in the volume dispensed to the patient beyond the specific patient volume can be dispensed with. If this is not the case, however, the method in accordance with the invention will be used.

The time at which the drain period is ended can depend on at least one parameter, with the parameter being able to be one or more of the following volumes: reached drain volume; flow rate during the drain period; and pressure in the abdominal cavity of the patient.

The switchover value at which the drain period is ended can amount to a specific percentage of the tidal outflow target or of the specific inflow volume, with provision preferably being made that the percentage lies in the range from above 0 to 60%, and preferably in the range from 10 to 50%, of the tidal outflow target or of the specific inflow volume.

Provision can furthermore be made that the permitted patient volume or the volume added during a filling period lies in the range from above 100 to 150%, preferably in the range from above 100 to 120%, and particularly preferably in the range from above 100 to 130%, of the specific patient volume or of the specific inflow volume.

BRIEF DESCRIPTION OF THE DRAWINGS

Further details and advantages of the invention will be explained in more detail with reference to an embodiment shown in the drawing.

There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
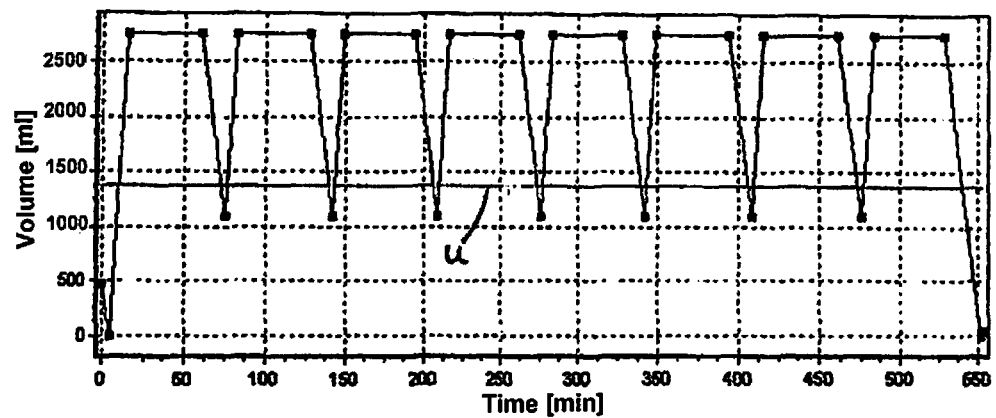
FIG. 1: time schedule of a tidal peritoneal dialysis treatment with a lower swichover point.
Figure 4:
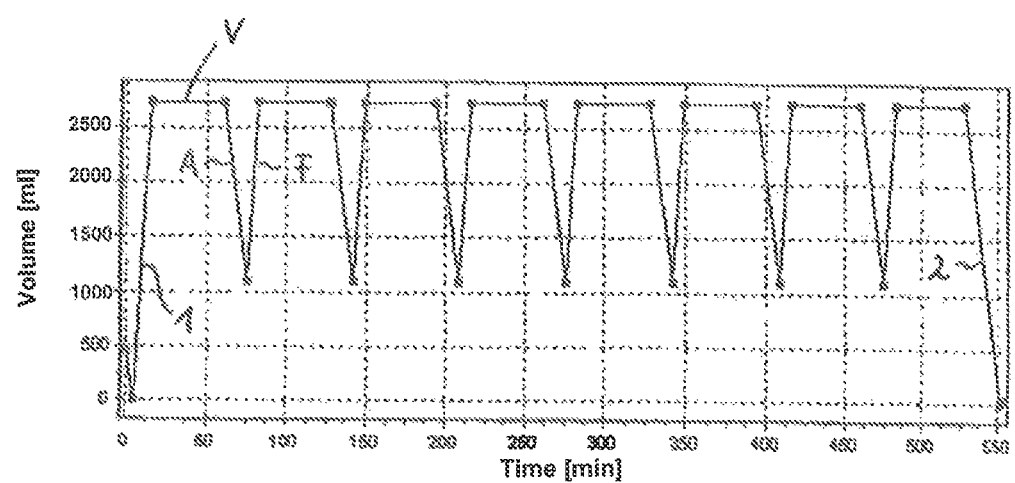
FIG. 4: time schedule of a tidal peritoneal dialysis treatment in accordance with the prior art.

FIG. 1 shows the time development of a tidal peritoneal dialysis treatment in accordance with FIG. 4 with a superimposed lower volume management limit in the form of the line U. This line represents the switchover point or the volume value on whose falling below a switchover to the next filling period takes place in the drain period in accordance with the operating mode in accordance with the invention. As can be seen from FIG. 1, this line is above the switchover points on a procedure in accordance with the prior art. The latter lie at a volume of 1100 ml in the embodiment shown here. The line U or the switchover points in accordance with the invention lie at a volume of 1400 ml or in a volume range of >1100 ml to 1400 ml. The volume values given are the volume of the dialysis solution in the abdominal cavity of the patient. The volume of the dialysis solution in the patient at the line U is called a permitted residual volume within the framework of the invention.

Figure 2:
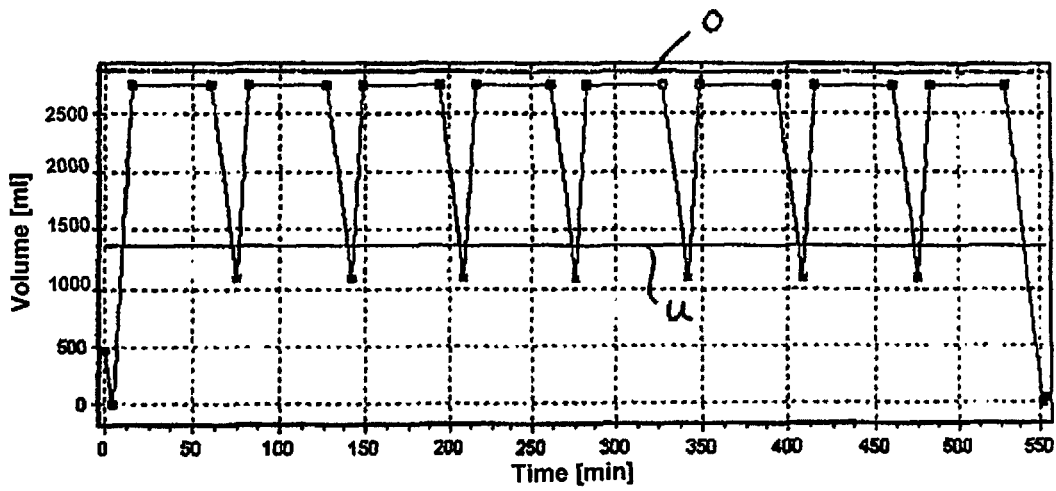
FIG. 2: time schedule of a tidal peritoneal dialysis treatment with an upper and a lower switchover point.

FIG. 2 shows the time development of a tidal peritoneal dialysis treatment in accordance with FIG. 1 with a superimposed upper volume management limit in the form of the line O. This line represents the switchover point or the volume value on whose reaching or exceeding an ending of the filling period and a start of the dwell period takes place. As can be seen from FIG. 2, this line O is above the upper switchover points (switchover to the dwell period) on a procedure in accordance with the prior art. The latter lie at a volume of 2700 ml in the embodiment shown here. The line O or the switchover points in accordance with the invention lie at a volume of 2900 ml or in a volume range of >2700 ml to 2900 ml. The volume values given are the volume of the dialysis solution in the abdominal cavity of the patient. The volume of the dialysis solution in the patient at the line O is called a permitted patient volume within the framework of the invention. FIG. 2 thus illustrates the additional volume toleration in the inflow, i.e. during the filling period.

Figure 3:
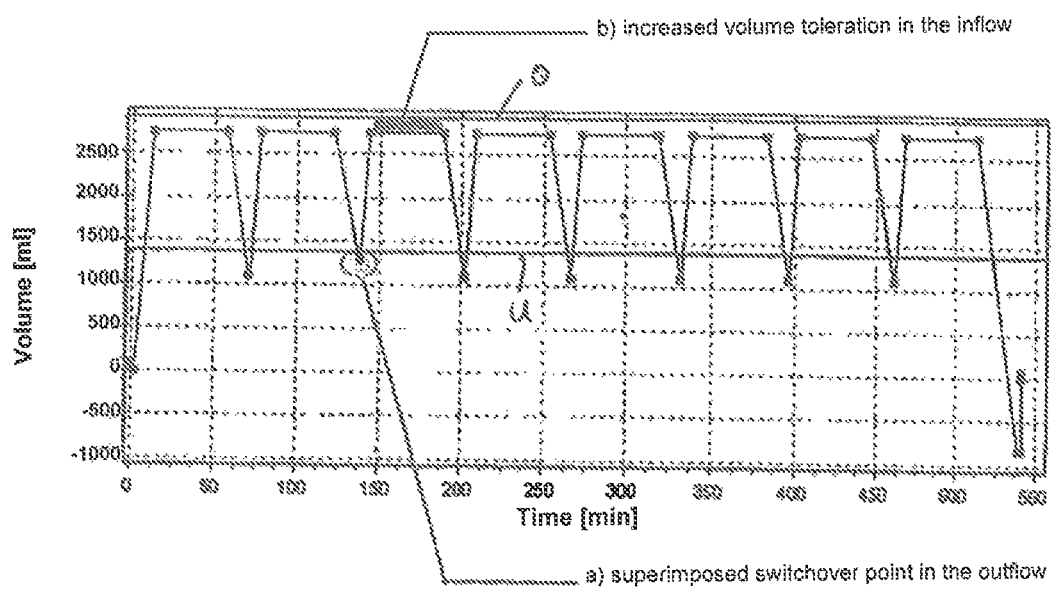
FIG. 3: time schedule of a tidal peritoneal dialysis treatment with a lower switchover point with a marking of the superimposed switchover point in the outflow and an increased volume toleration in the inflow.

FIG. 3 illustrates that the tidal outflow target (volume 1100 ml) in the second cycle is not reached or is at least not reached within a specific time period because the outflow speed is comparatively small as can be recognized by the lower inclination of the line.

This has the result that the draining is aborted at the time marked by a) before the tidal outflow target is reached and a switchover to a new filling period is made.

An increased residual volume is thus accepted. In order nevertheless to be able to dispense a sufficient volume of dialysis solution, an exceeding of the specific patient volume to the amount of 2700 ml is accepted in the following filling period and the filling period is extended until the patient volume, i.e. the volume of dialysis solution in the patient, amounts to 2900 ml.

If filling took place in this filling period only up to the specific patient volume to the amount of 2700 ml, only a smaller volume of dialysis solution could be dispensed overall in the predetermined treatment time or one or more further cycles would be necessary on an exceeding of the predetermined treatment time.

It is possible with the volume management in accordance with the invention already to fix a higher outflow volume in the prescription and thus to achieve a more efficient use of the dialysis solution.

The necessity of carrying out one or more additional cycles can be omitted with the procedure in accordance with the invention. Furthermore, a shortening of the dwell times can be avoided and the patient can nevertheless end the treatment at the provided time.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An apparatus for carrying out a tidal peritoneal dialysis treatment of a patient that includes a sequence of cycles each having a filling period, a dwell period, and a drain period, said apparatus comprising:

a cycler configured for filling an abdominal cavity of the patient with a specific inflow volume of a fresh dialysis solution up to a reaching of a specific patient volume in the filling period, and for emptying a consumed dialysis solution from the abdominal cavity of the patient up to a reaching of a specific tidal outflow target in the drain period, the specific tidal outflow target including a removed volume of the consumed dialysis solution, the cycler configured to deliver to the patient a predefined patient volume of the dialysis solution during a specific treatment time; and a processor which controls the cycler in at least one operating mode such that the drain period of one of the sequence of cycles is ended before reaching the specific tidal outflow target so that a permitted residual volume remains in the abdominal cavity, and then a switch is made to the filling period, and in that the filling period is carried out such that a filling volume of the patient lies at a permitted patient volume above the specific patient volume on the completion of the filling period, the processor being configured such that a switchover value at which the drain period is ended is associated with the specific tidal outflow target, which is a specific percentage of the tidal outflow target, said specific percentage being in a range from 10 to 50% of the tidal outflow target.

2. The apparatus in accordance with claim 1, wherein at least one of the permitted residual volume and the permitted patient volume can be adjusted.

3. The apparatus in accordance with claim 1, wherein the permitted residual volume and the permitted patient volume can be adjusted independently of one another.

4. The apparatus in accordance with claim 1, wherein the processor is configured such that selection of the at least one operating mode depends on the reaching of the specific tidal outflow target.

5. The apparatus in accordance with claim 1, wherein the processor is configured such that a time at which the drain period is ended depends on at least one parameter selected from the group consisting of achieved volume, flow rate during the drain period, and pressure in the abdominal cavity of the patient.

6. The apparatus in accordance with claim 1, wherein the processor is configured such that the permitted patient volume or the volume added within the course of the filling period lies in a range from above 100 to 150% of the specific patient volume or of the specific inflow volume.

7. The apparatus according to claim 6, wherein the range is from above 100 to 130% of the specific patient volume or of the specific inflow volume.

8. The apparatus according to claim 7, wherein the range is from above 100 to 120% of the specific patient volume or of the specific inflow volume.

9. A method of carrying out a tidal peritoneal dialysis treatment of a patient that includes a sequence of cycles each having a filling period, a dwell period, and a drain period, said method comprising:

a filling of the abdominal cavity of the patient with a specific inflow volume of a fresh dialysis solution up to a reaching of a specific patient volume taking place during the filling period, and an emptying of a consumed dialysis solution from the abdominal cavity of the patient up to a reaching of a specific tidal outflow target taking place in the drain period, the specific tidal outflow target including a removed volume of the consumed dialysis solution, delivering to the patient a predefined patient volume of the dialysis solution during a specific treatment time, with the drain period being ended before reaching the specific tidal outflow target in at least one operation mode so that a permitted residual volume remains in the abdominal cavity, with a switching over into the filling period, the filling period being carried out such that a filling volume of the patient lies above the specific patient volume on an ending of the filling period at a permitted patient volume, and with a switchover value at which the drain period is ended being associated with the specific tidal outflow target, which is a specific percentage of the tidal outflow target, said specific percentage being in a range from 10 to 50% of the tidal outflow target.

10. The method in accordance with claim 9, wherein at least one of the permitted residual volume and the permitted patient volume can be adjusted.

11. The method in accordance with claim 9, wherein the permitted residual volume and the permitted patient volume can be set independently of one another.

12. The method in accordance with claim 9, wherein the selection of the operating mode depends on the reaching of the specific tidal outflow target.

13. The method in accordance with claim 9, wherein a time at which the drain period is ended depends on at least one parameter selected from the group consisting of reached drain volume, flow rate during the drain period, and pressure in the abdominal cavity of the patient.

14. The method in accordance with claim 9, wherein the permitted patient volume or the inflow volume added within the course of the filling period lies in a range from above 100 to 150% of the specific patient volume or of the specific inflow volume.

15. The method according to claim 14, wherein the range is from above 100 to 130% of the specific patient volume or of the specific inflow volume.

16. The method according to claim 15, wherein the range is from above 100 to 120% of the specific patient volume or of the specific inflow volume.

* * * * *